(12) United States Patent
Suddaby

(10) Patent No.: US 6,958,077 B2
(45) Date of Patent: Oct. 25, 2005

(54) INFLATABLE NUCLEAR PROSTHESIS

(76) Inventor: Loubert Suddaby, 76 Tanglewood Dr., Orchard Park, NY (US) 14127

(*) Notice: Subject to any disclaimer, the term of this patent is extended or adjusted under 35 U.S.C. 154(b) by 52 days.

(21) Appl. No.: 10/628,355

(22) Filed: Jul. 29, 2003

(65) Prior Publication Data
US 2005/0027358 A1   Feb. 3, 2005

(51) Int. Cl.$^7$ .................................................. A61F 2/44
(52) U.S. Cl. ................................................... 623/17.11
(58) Field of Search ........................ 623/17.11, 23.54, 623/23.57, 23.59, 23.58, 23.62, 23.76, 16.11, 623/17.12

(56) References Cited

U.S. PATENT DOCUMENTS

| | | | |
|---|---|---|---|
| 3,875,595 A | 4/1975 | Froning | |
| 5,192,326 A * | 3/1993 | Bao et al. | 623/17.12 |
| 5,571,189 A | 11/1996 | Kuslich | |
| 5,674,295 A | 10/1997 | Ray et al. | |
| 6,022,376 A * | 2/2000 | Assell et al. | 623/17.16 |
| 6,443,988 B2 * | 9/2002 | Felt et al. | 623/17.12 |
| 6,632,235 B2 * | 10/2003 | Weikel et al. | 606/192 |
| 6,805,697 B1 * | 10/2004 | Helm et al. | 606/92 |

* cited by examiner

Primary Examiner—Pedro Philogene
(74) Attorney, Agent, or Firm—Shoemaker and Mattare

(57) ABSTRACT

The nucleus of an intervertebral disc is replaced with a construct including a distendable sack or balloon which is inflated with a hardenable material and is detached in situ when the injected material has hardened. Alternatively, two nested balloons may be inserted, and then filled with materials which have different hardnesses when cured, to simulate a natural disc.

5 Claims, 4 Drawing Sheets

INFLATABLE NUCLEAR PROSTHESIS

BACKGROUND OF THE INVENTION

This invention relates to orthopedic surgery, more particularly to a prosthetic nuclear replacement for a damaged intervertebral disc, and a surgical procedure for implanting the construct in the intervertebral disc space.

The normal intervertebral disc has an outer fibrous ring, constituted mainly of collagen fibers, which strongly binds the vertebral elements together. This fibrous outer layer, or annulus, encircles a soft gel-like matrix, or nucleus, which serves both as a cushion and as a mobile and compressible element that allows motion to occur between the vertebral bodies above and below the intervertebral disc. This gel matrix is 95% water. The types of motion that can occur at the level of the intervertebral disc include flexion, extension, lateral bending and varying degrees of torsion or rotation.

In the course of a day, the normal intervertebral disc may encounter various combinations of these bending or twisting motions several thousand times. As a consequence of such repetitive motion, natural discs deteriorate over time, much as the padded cushion on a well-used chair might do.

The effect of this deterioration is a loss of water content of the gel matrix of the nucleus and a concomitant compacting of its fibers with a resultant loss of disc space height which in turn causes a loosening of the surrounding support ligaments of the spine and the development of what is termed degenerative instability. This instability results in a pathologic excess of movement at the intervertebral disc space that further accentuates the degeneration of both the nucleus and the annulus of the disc. With continued deterioration, the annulus of the disc can bulge or even develop radial tears that allow the inner nuclear material to protrude or even extrude from the disc space. This bulging of the annulus or protrusion of the nucleus can compress nerves and cause disabling sciatic pain. Distension or bulging of the annulus alone is frequently sufficient to produce disabling back pain because of compression or inflammation of free nerve endings present in the outer annulus of the disc.

The time-honored method of addressing degenerative lumbar instability resulting from severely damaged intervertebral discs has been to remove the damaged disc completely and fuse the two adjacent vertebral bones to eliminate pathological motion. While the approach does well at eliminating pathological motion, it also prevents any natural motion at that segment. The consequence of eliminating natural motion at a single segment generally is that greater degrees of stress occur above or below that segment. This in turn accelerates degeneration of the neighboring intervertebral spaces, often necessitating additional fusion surgeries.

It would be desirable, therefore, to preserve natural motion at every disc space and thus eliminate the degenerative domino effect that discectomy and fusion seems to produce. Since the earliest pathologic change evident in a degenerative disc is loss of water content with concomitant loss of disc space height, maintenance of disc space height seems critical for maintaining the way opposing vertebral surfaces alter position with each other during bending and twisting. Indeed, loss of disc space height seems to be the more crucial early feature of degenerative instability. With degenerative instability the ligaments may ultimately become so lax that buckling of the ligaments occurs, or even pathologic slippage of the spine (spondylolithesis) may result. Preserving disc space height is therefore important in preventing secondary degenerative changes that occur as a consequence of loss of the disc space height from mechanical damage or dessication due to aging.

An intervertebral disc nuclear prosthesis ought, ideally, to restore and preserve disc space height while permitting sufficient natural motion (flexion, extension, lateral bending and rotation) to prevent excessive stresses on spinal segments above and below the prosthesis. Natural motion may also play a role in the health of the annulus and surrounding ligaments, much as natural stresses play a role in the maintenance of strength and density of normal living bone.

Many synthetic structures have been used as intervertebral disc implants, but few materials are durable enough to withstand the tremendous and repetitive forces a natural disc must withstand. In addition, the majority of intervertebral implants fail to restore and maintain sufficient disc space height to keep spinal support ligaments taut. Maintenance of a physiologic degree of tautness seems crucial to the long-term viability of spinal support ligaments.

Kuslich, in U.S. Pat. No. 5,571,189, describes an expandable porous fabric implant designed to stabilize a spinal segment. The fabric is porous and packed with biologic material which favors fusion of the interspace rather than functional mobility. It is packed with material which stabilizes a spinal segment by allowing ingrowth of bone and fibrous issues through pores on its surface.

In U.S. Pat. No. 5,674,295, Ray describes a pillow-shaped prosthetic spinal disc nucleus body made of a hydrogel core and a flexible constraining jacket which permits the hydrogel core to expand and contract. The constraining jacket is also porous, allowing entry and egress of fluids. The jacket is not filled with a hardenable material, since significant expansion and contraction is a pivotal feature to the biologic function of the prosthesis he describes.

U.S. Pat. No. 3,875,595 to Froning describes a bladder-like prosthesis which is inflated with liquid or plastic, but which requires a valve as the material is non-hardenable and could potentially leak from the retaining bladder, causing the prosthesis to collapse.

SUMMARY OF THE INVENTION

An object of the invention is provide an intervertebral disc nuclear replacement prosthesis that simultaneously restores sufficient disc space height and mobility to provide a semblance of functional normalcy and to reduce or eliminate abnormal stresses on adjacent intervertebral segments.

To achieve these objectives, an inflatable sack or balloon is inserted into an intervertebral disc in which complete nuclectomy has been performed. The balloon is first inflated with radioopaque contrast material under fluoroscopic observation and the volume of contrast material necessary to restore disc space height as the balloon distends is recorded. The contrast material is then aspirated and an identical volume of hardenable material is injected into the balloon and allowed to harden. The balloon and its contents are then detached from the inflating apparatus and left in situ to form a functional intervertebral endoprosthesis. Because of its deformable and distensible nature, the balloon conforms to and forms a perfect cast of the vertebral end plates it comes in contact with, allowing for a completely customized endoprosthesis in every case.

The balloon may be made so as to have non-uniform surface characteristics. For example, the portion in contact with the end plates may be made of an inert material (so that movement of the end plates referable to the endoprosthesis can occur) while the lateral aspect of the balloon may be made of material favoring tissue ingrowth, to aid in anchoring the endoprosthesis to the annulus and to prevent expulsion of the implant under physiologic loads, once post-surgical healing has occurred.

The term "balloon" as used herein is intended to mean a thin, flexible, liquid impervious container which can be filled with liquid under pressure; the material from which the balloon is made, while flexible, need not be highly elastic.

Suitable materials for the walls of the balloon or sack include Kevlar, polypropylene or any of a variety of plastics or fabrics having either elastic or non-elastic properties, provided they are sufficiently pliable to conform with end plate surfaces, and have sufficient tensile strength to allow for pressurized restoration of disc space height. The material should also be sufficiently non-porous so as to prevent leakage of materials when distended under pressure.

While in its most basic iteration a single balloon is used, it is also recognized that balloons having two or more compartments might be employed to allow for more sophisticated applications. For example, a balloon may be placed within a balloon, the inner balloon being filled with a hardenable material that retains viscoelastic properties and the surrounding outer balloon being filled with a hardenable material that is less elastic or non-elastomeric. This way, the functional properties of a normal disc can be more correctly replicated.

Suitable materials to inflate the chamber or chambers include any hardenable material that can be injected into the balloon, in a liquid or semi-solid state, such that disc space height can be restored as the material is injected under pressure. Once disc space height is restored, the material then changes state, retaining sufficient functional integrity to resist disruption or dissolution when exposed to the varying loads and forces experienced by a natural disc. In the final hardened state, the material may retain viscoelastic or non-elastic properties, depending on the desire of the implanting surgeon who would select the material to be injected. These materials include polymethyl methacrylate, polycarbonate, plastics, various polymerizing resins or indeed any material capable of being injected in a liquid or semi-solid state and then capable of assuming or retaining a functional structural shape as determined by the balloon or sack into which it is injected.

Because of the distensible nature of the balloon, the construct is anticipated to conform to the unique shape of the disc and its adjacent end plates and the construct is expect to self-center within the disc space by virtue of the convex shape most end plates exhibit.

BRIEF DESCRIPTION OF THE DRAWINGS

In the accompanying drawings.

DESCRIPTION OF THE PREFERRED EMBODIMENTS

Figure 1:
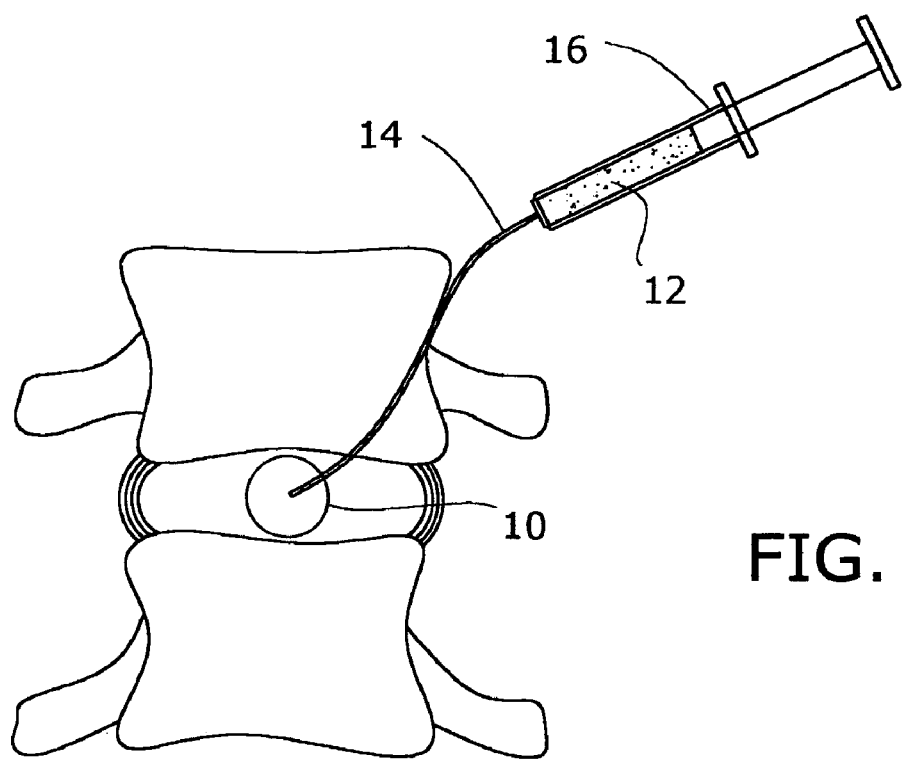
FIG. 1 is a diagrammatic dorsal view of a balloon which has been implanted into an intervertebral disc which has undergone nuclectomy.

In a first embodiment of the invention, a deflated balloon 10 (FIG. 1) is placed within an intervertebral disc in which a cavity has been formed by a complete nuclectomy. The balloon is then inflated with a liquid contrast medium (not shown), while the area is observed by the surgeon, who terminates inflation when the desired distension is observed. Then the contrast medium is completely withdrawn, and the withdrawn volume is noted.

Figure 2:
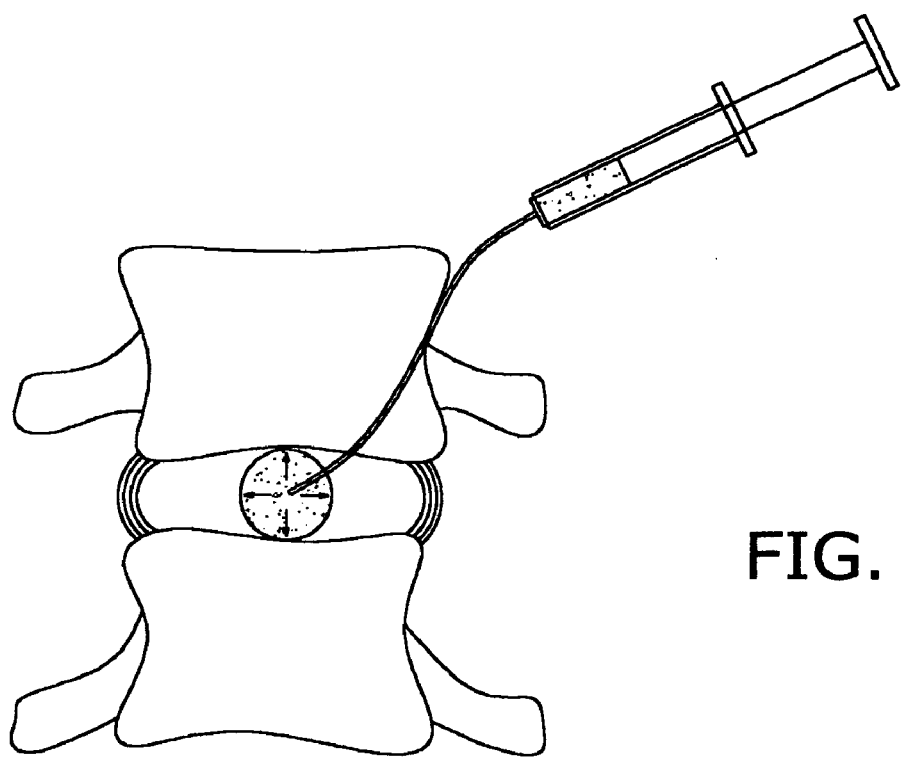
FIG. 2 shows the balloon being enlarged by insufflation with a hardenable material in liquid form.
Figure 3:
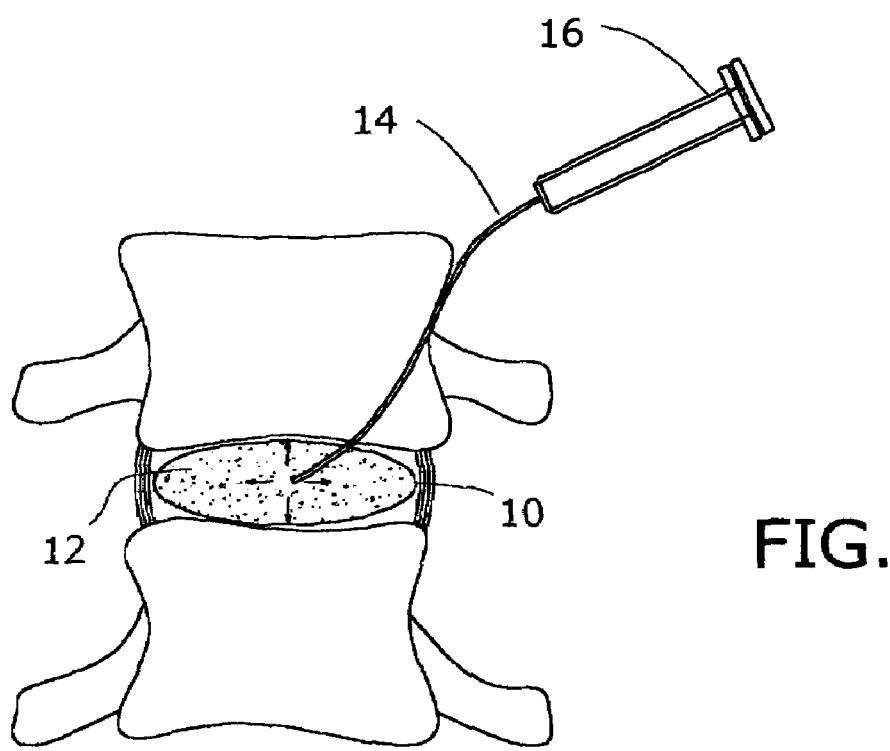
FIG. 3 demonstrates restoration of disc space height and replacement of the nucleus by the inflated balloon as it conforms to the surrounding confines.

Next, an identical volume of a hardenable material 12 in liquid form is injected through a conduit 14 connected to a source of the material under pressure, for example a syringe 16. As material enters the balloon, the balloon expands as suggested by the arrows in FIGS. 2 and 3. Note that the annular fibers become more taut as the pressure increases the separation distance between the vertebrae.

Figure 4:
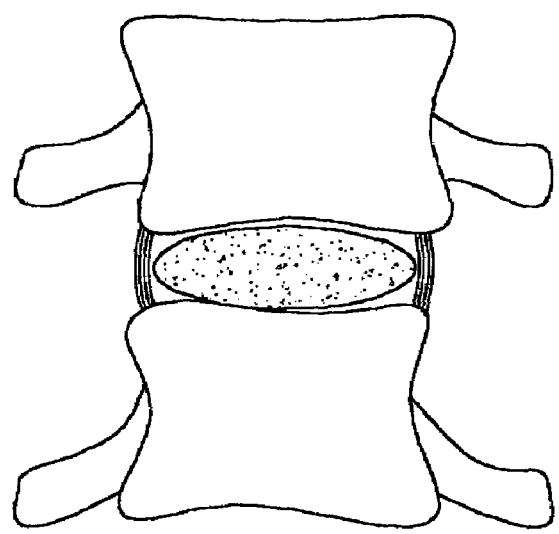
FIG. 4 shows the balloon and its contents, which have now hardened and have been detached and left in situ.
Figure 5:
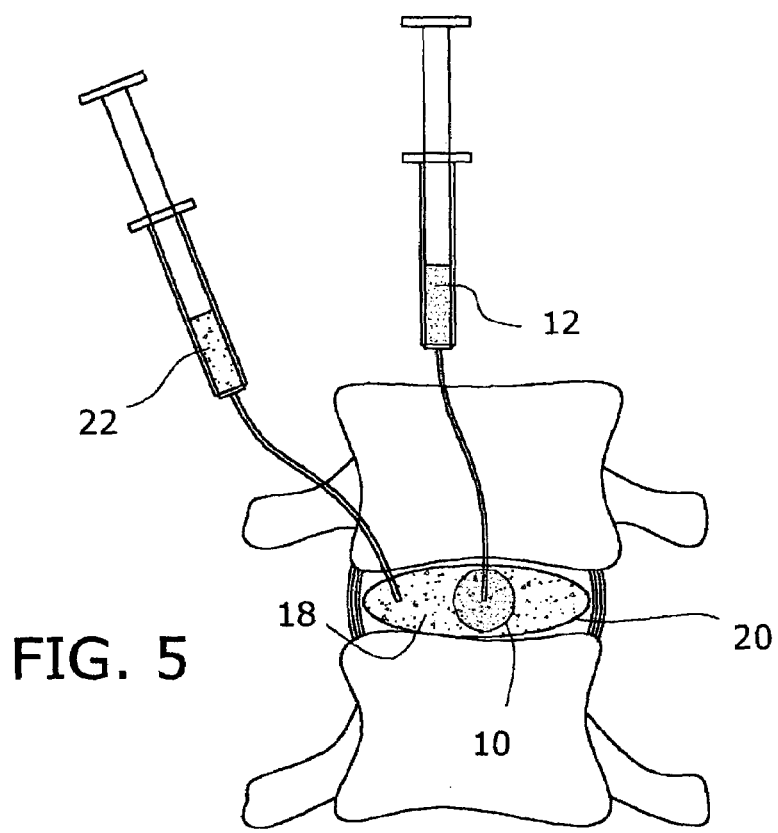
FIG. 5 shows a dual compartment balloon in which an inner and an outer compartment are insufflated with materials having different elastomeric properties when in their hardened states.
Figure 6:
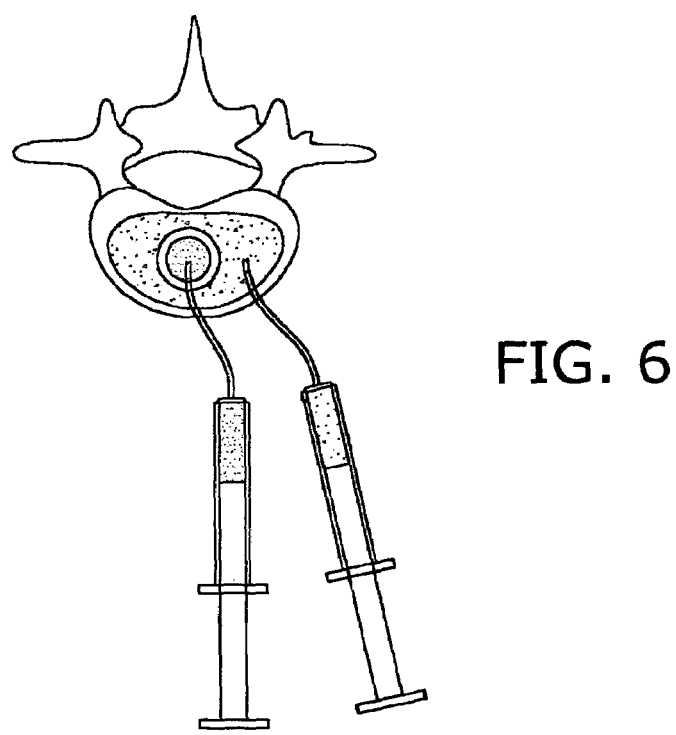
FIG. 6 is an axial view of the construct shown in FIG. 5.
Figure 7:
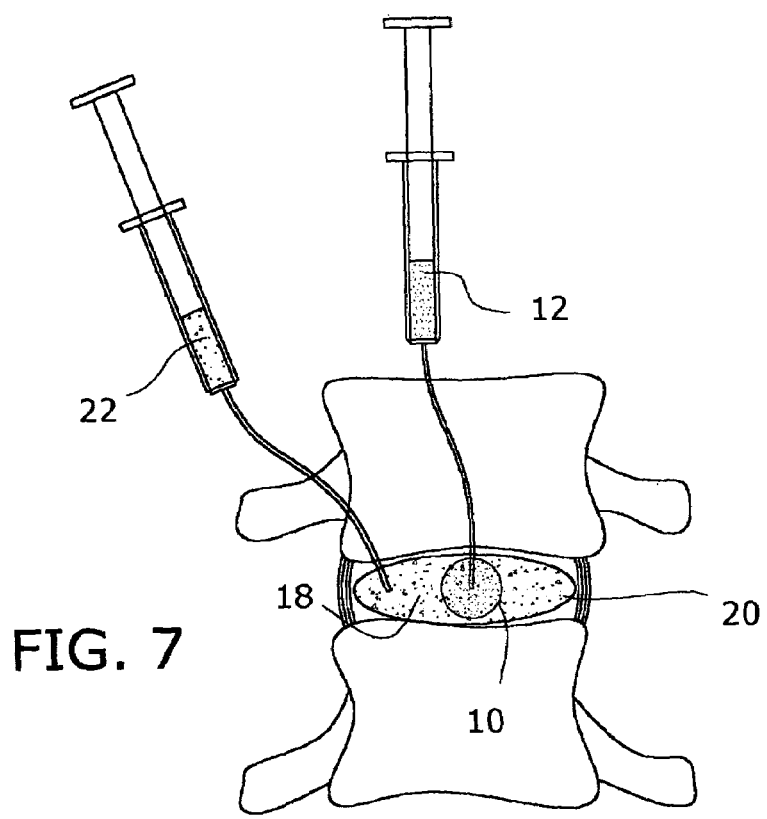
FIG. 7 shows a dual compartment balloon as in FIG. 5, prior to insufflation.
Figure 8:
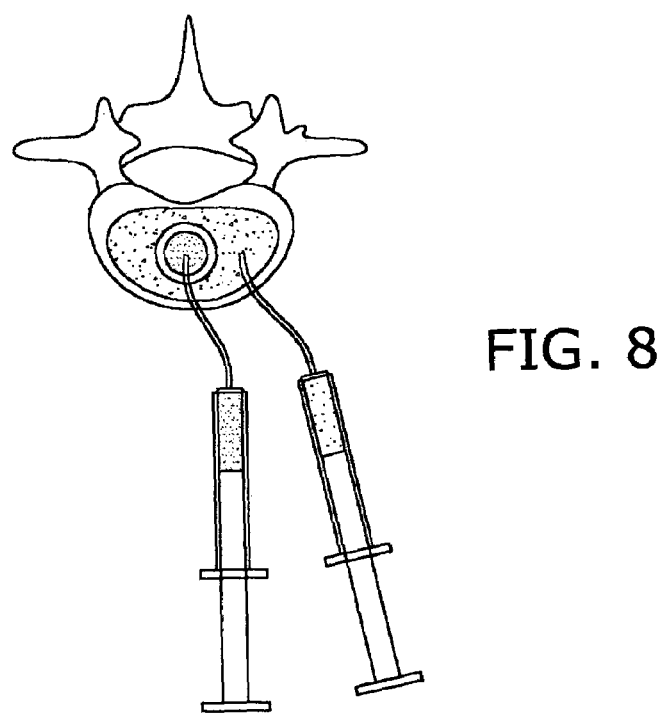
FIG. 8 is an axial view of the construct shown in FIG. 7.

Once the predetermined volume of the hardenable material has been injected, it is allowed or induced to harden. When the material has hard hardened at least to the point that is will no longer flow, the pressure source is withdrawn (FIG. 4), leaving the filled balloon in place within the disc.

In a second embodiment of the invention, two balloons, one inside the other, are inserted into the disc. Using volume measuring and filling techniques similar to those described above, the inner balloon 10 is filled with a first liquid material 12, and the chamber 18 formed between the inner balloon 10 and the outer balloon 20 is filled with a second hardenable material 22 in liquid form. The first liquid material 12 is preferably hardenable, but to a substantially lesser hardness that the outer material, so that cured construct is relatively soft on the inside, and relatively harder on the outside, like a natural disc. The inner portion thus retains greater elastic properties to provide a cushioning effect, whereas the outer portion has little or no elasticity, to preserve the strength and integrity of the entire construct.

Since the invention is subject to modifications and variations, it is intended that the foregoing description and the accompanying drawings shall be interpreted as only illustrative of the invention defined by the following claims.

I claim:

1. A method of replacing a natural vertebral disc, said method comprising steps of
   removing at least a portion of the vertebral disc, leaving an intervertebral space between opposed vertebral end plates,
   inserting a first outer deflated balloon into said space,
   placing a second inner deflated balloon within said first balloon, thus defining a chamber between said first balloon and said second balloon,
   injecting a first material in liquid form into said inner balloon,
   injecting a second hardenable material in liquid form into said chamber, and causing or allowing said hardenable materials to harden, without withdrawing either balloon, thereby forming a stable mass conforming in shape to said intervertebral space.

2. The method of claim 1, wherein said first material is hardenable.

3. The method of claim 2, wherein said first hardenable material and said second hardenable material have, when hardened, different physical properties.

4. The method of claim 3, wherein said second hardenable material is harder than said first hardenable material, when both have hardened.

5. The method of claim 2, wherein said first hardenable material has greater elasticity than said second hardenable material, when both have hardened.

* * * * *